US009127028B2

(12) United States Patent
Kelly et al.

(10) Patent No.: US 9,127,028 B2
(45) Date of Patent: Sep. 8, 2015

(54) SUBSTRATES FOR CHROMOGENIC DETECTION AND METHODS OF USE IN DETECTION ASSAYS AND KITS

(75) Inventors: Brian Daniel Kelly, Tucson, AZ (US); Christopher Bieniarz, Tucson, AZ (US); Hiro Nitta, Oro Valley, AZ (US); Fabien Gaire, Starnberg (DE)

(73) Assignee: Ventana Medical Systems, Inc., Tucson, AZ (US)

( * ) Notice: Subject to any disclaimer, the term of this patent is extended or adjusted under 35 U.S.C. 154(b) by 196 days.

(21) Appl. No.: 13/809,354

(22) PCT Filed: Aug. 12, 2011

(86) PCT No.: PCT/US2011/047613
§ 371 (c)(1),
(2), (4) Date: Jan. 9, 2013

(87) PCT Pub. No.: WO2012/024185
PCT Pub. Date: Feb. 23, 2012

(65) Prior Publication Data
US 2013/0115593 A1    May 9, 2013

Related U.S. Application Data

(60) Provisional application No. 61/374,087, filed on Aug. 16, 2010.

(51) Int. Cl.
| C07F 9/12 | (2006.01) |
| C12Q 1/70 | (2006.01) |
| C07F 9/6503 | (2006.01) |
| G01N 21/78 | (2006.01) |

(52) U.S. Cl.
CPC ............ *C07F 9/65035* (2013.01); *G01N 21/78* (2013.01)

(58) Field of Classification Search
CPC .................................................. C07F 9/65035
See application file for complete search history.

(56) References Cited

U.S. PATENT DOCUMENTS

| 4,120,956 A | 10/1978 | Maurer et al. |
| 4,711,955 A | 12/1987 | Ward et al. |
| 4,772,961 A | 9/1988 | Ichinoi |
| 4,888,278 A | 12/1989 | Singer et al. |
| 5,258,507 A | 11/1993 | Cruickshank et al. |
| 5,328,824 A | 7/1994 | Ward et al. |
| 5,427,932 A | 6/1995 | Weier et al. |
| 5,447,841 A | 9/1995 | Gray et al. |
| 5,472,842 A | 12/1995 | Stokke et al. |
| 5,800,988 A | 9/1998 | Casterman et al. |
| 5,840,526 A | 11/1998 | Casterman et al. |
| 5,874,541 A | 2/1999 | Casterman et al. |
| 6,005,079 A | 12/1999 | Casterman et al. |
| 6,015,695 A | 1/2000 | Casterman et al. |
| 6,280,929 B1 | 8/2001 | Gray et al. |
| 6,942,970 B2 | 9/2005 | Isola et al. |
| 7,695,929 B2 | 4/2010 | Kosmeder et al. |
| 7,812,140 B2 | 10/2010 | Banning et al. |
| 2001/0051342 A1 | 12/2001 | Farrell |
| 2006/0246523 A1 | 11/2006 | Bieniarz et al. |
| 2006/0246524 A1 | 11/2006 | Bauer et al. |
| 2007/0117153 A1 | 5/2007 | Bieniarz et al. |
| 2008/0057513 A1 | 3/2008 | Farrell |
| 2008/0249290 A1 | 10/2008 | Banning et al. |
| 2008/0305497 A1 | 12/2008 | Kosmeder et al. |
| 2011/0002345 A1 | 1/2011 | Bian et al. |
| 2011/0144332 A1 | 6/2011 | Ying et al. |
| 2012/0070862 A1 | 3/2012 | Alexander et al. |

FOREIGN PATENT DOCUMENTS

WO        2007021966 A1    2/2007

OTHER PUBLICATIONS

Hu et al. CAS Accession No. 2000:189793.*
"Colorimetric Alkaline Phosphatase and Peroxidase Substrate Detection Systems". Sigma-Aldrich Biofiles, vol. 3.4., No. 6, Jun. 1, 2008, XP002662327.
Pinkel et al, "Cytogenetic analysis using quantitative, high-sensitivity, fluorescence hybridization," Proc. Natl. Acad. Sci, May 1986, vol. 83, p. 2934-2938.
Poddighe et al, "Human papilloma virus detection by in situ hybridisation signal amplification based on biotinylated tyramine deposition," J. Clin. Pathol. Mol. Pathol., 1996, vol. 49, p. M340-M344.
Burstone, J. Histochem. Cytochem. 6 322-39 (1958).
Lichter et al, "Rapid detection of human chromosome 21 aberrations by in situ hybridization," Proc. Natl. Acad. Sci., Dec. 1988, vol. 85, p. 9664-9668.
Pinkel et al, "Fluorescence in situ hybridization with human chromosome-specific libraries: Detection of trisomy 21 and translocations of chromosome 4," Proc. Natl. Acad. Sci., Dec. 1988, vol. 85, p. 9138-9142.
Tanner et al, "Chromogenic in Situ Hybridization A Practical Alternative for Fluorescence in Situ Hybridization to Detect HER-2/neu Oncogene Amplification in Archival Breast Cancer Samples," American Journal of Pathology, Nov. 2000, vol. 157, No. 5, p. 1467-1472.

* cited by examiner

*Primary Examiner* — Joseph Kosack
(74) *Attorney, Agent, or Firm* — Charney IP Law LLC; Thomas M. Finetti

(57) ABSTRACT

Embodiments of substrates and processes for chromogenic detection, and in particular pyrazolyl dihydrogen phosphate compounds, are disclosed.

27 Claims, 9 Drawing Sheets

1

Calu-3
Amplified HER2 Gene

MCF7
Non-amplified HER2 Gene

Clinical Case B
Amplified HER2 Gene

Clinical Case A
Non-amplified HER2 Gene

Clinical Case C
Tumor Heterogeneity

SUBSTRATES FOR CHROMOGENIC DETECTION AND METHODS OF USE IN DETECTION ASSAYS AND KITS

CROSS REFERENCE TO RELATED APPLICATION

This application claims the benefit of the earlier filing date of U.S. Provisional Application No. 61/374,087, which was filed on Aug. 16, 2010. The entire disclosure of the provisional application is considered to be part of the disclosure of the following application and is hereby incorporated by reference.

FIELD

The present disclosure relates to substrates and processes for chromogenic detection, and in particular to pyrazolyl dihydrogen phosphate compounds.

BACKGROUND

The diagnosis of disease based on the interpretation of tissue or cell samples taken from a diseased organism has expanded dramatically over the past few years. In addition to traditional histological staining techniques and immunohistochemical assays, in situ techniques such as in situ hybridization and in situ polymerase chain reaction are now used to help diagnose disease states in humans. Thus, there are a variety of techniques that can assess not only cell morphology, but also the presence of specific macromolecules within cells and tissues.

Chromogenic alkaline phosphatase (AP) detection on tissue has commonly been performed by a combination of a substituted naphthol AS phosphate and a diazonium salt. This methodology was introduced by Burstone in the late 1950's. See Burstone, *J. Histochem. Cytochem.* 6 322-39 (1958). The technique involves the liberation of naphthol by AP, which then reacts with a diazonium salt to generate an insoluble azo dye that precipitates at the epitope site.

Chromogenic techniques have been limited due to a limited number of chromogenic substrates that impart different colors. Accordingly, what is needed in the art are chromogenic substrates that provide new colors for use in immunohistochemical and hybridization assays. The addition of novel chromogenic substrates provides for, for example, the multiplexing of different targets that are identified by different color deposits, all of which are identifiable on a single tissue on a single slide.

SUMMARY

Disclosed herein are embodiments of substrates and processes for chromogenic detection, and in particular pyrazolyl dihydrogen phosphate compounds.

The present disclosure is not limited to particular pyrazolyl dihydrogen phosphate compounds. In certain embodiments, the compounds are described by the following formula:

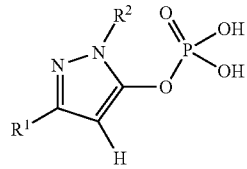

including salts, and prodrugs thereof; and including both R and S enantiomeric forms and racemic mixtures thereof.

In some embodiments, $R^1$ is hydrogen, a halogen (e.g., chlorine, fluorine, bromine, iodine), a saturated or unsaturated aliphatic group of any desired length, or an aryl group of any desired size.

In some embodiments, $R^2$ is hydrogen, a saturated or unsaturated aliphatic group of any desired length, or an aryl group of any desired size.

As used herein, the term "aliphatic" represents the groups commonly known as alkyl (e.g., substituted or unsubstituted), alkenyl (e.g., substituted or unsubstituted), alkynyl (e.g., substituted or unsubstituted), alicyclic (e.g., substituted or unsubstituted).

As used herein, the term "substituted aliphatic" refers to an aliphatic group having any desired number of carbon atoms (e.g., 100, 80, 75, 50, 40, 30, 35, 30, 25, 24, 23, 22, 21, 20, 19, 18, 17, 16, 15, 14, 13, 12, 11, 10, 9, 8, 7, 6, 5, 4, 3, 2), where at least one of the aliphatic hydrogen atoms has been replaced by a halogen (e.g., chlorine, bromine, fluorine, iodine), an amino, a hydroxy, an alkoxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.).

The term "alkyl" is art-recognized and refers to saturated aliphatic groups, including straight-chain alkyl groups, branched-chain alkyl groups, cycloalkyl(alicyclic) groups, alkyl substituted cycloalkyl groups, and cycloalkyl substituted alkyl groups.

The term "substituted alkyl" is art-recognized and refers to an alkyl moiety having a substituent replacing a hydrogen atom on one or more carbon atoms of the hydrocarbon backbone. Such substituents can include, for example, alkenyl, alkynyl, halogen (e.g., chlorine, bromine, fluorine, iodine), hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "aryl" represents a single aromatic ring such as a phenyl ring, or two or more aromatic rings that are connected to each other (e.g., bisphenyl) or fused together (e.g., naphthalene or anthracene).

As used herein, the term "substituted aryl" refers to an aromatic ring or fused aromatic ring system where at least one of the hydrogen atoms on a ring carbon has been replaced by a halogen (e.g., chlorine, bromine, fluorine, iodine), an amino, a hydroxy, an alkoxy, a nitro, a thio, a ketone, an aldehyde, an ester, an amide, a lower aliphatic, a substituted lower aliphatic, or a ring (e.g., aryl, substituted aryl, cycloaliphatic, or substituted cycloaliphatic). Examples of such include, but are not limited to, hydroxyphenyl and the like.

In some embodiments, $R^1$ is hydrogen.
In some embodiments, $R^1$ is $CH_3$.
In some embodiments, $R^2$ is

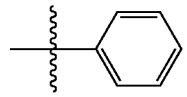

(phenyl).

In some embodiments, $R^2$ is hydrogen.

In some embodiments, the pyrazolyl dihydrogen phosphate compound is a salt that is further described by the following formula:

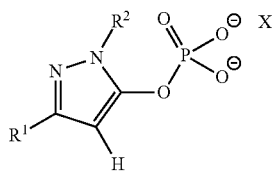

wherein X represents any ion having a positive charge.

In some embodiments, X is two of any monovalent positive ions (e.g., 2 $Na^+$, 2 $K^+$, 2 $NH_4^+$, etc.).

In some embodiments, X is any divalent positive ion (e.g., $Mg^{2+}$).

In some embodiments, the pyrazolyl dihydrogen phosphate compound is 3-methyl-1-phenyl-1H-pyrazol-5-yl dihydrogen phosphate:

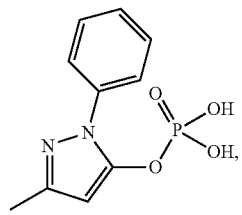 [SMILES: Cc1cc(OP(=O)(O)O)n(-c2ccccc2)n1]

including salts and prodrugs thereof; and including both R and S enantiomeric forms and racemic mixtures thereof.

In some embodiments, the compound is a substrate for a phosphatase. In some embodiments, the compound forms a gold or yellow precipitate in the presence of a phosphatase and a diazonium salt. In some embodiments, the diazonium salt is 4-(benzoylamino)-2,5-diethoxybenzenediazo tetrachlorozincate (Fast Blue BB).

Embodiments of kits comprising a compound as described above and a diazonium salt are disclosed. In some embodiments, the kits further comprise an enzyme that reacts with said compound. In some embodiments, the enzyme is a phosphatase. In some embodiments, the diazonium salt is 4-(benzoylamino)-2,5-diethoxybenzenediazo tetrachlorozincate (Fast Blue BB). In some embodiments, the enzyme is conjugated to a hapten. In some embodiments, the enzyme is conjugated to an antigen-binding protein. In some embodiments, the antigen-binding protein binds to a hapten. In some embodiments, the enzyme is conjugated to a nucleic acid. In some embodiments, the substrate compound is as follows.

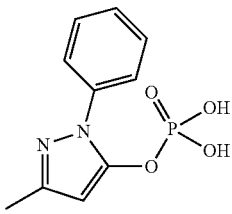

In some embodiments, methods of detecting a target in a biological sample include: contacting said sample with a detection reagent comprising an enzyme that reacts with a compound according to claim 1, wherein said detection reagent directly or indirectly binds to said target, a compound according to claim 1, and a diazonium salt, wherein said enzyme acts on said compound in the presence of said diazonium salt to produce a colored compound; and detecting the presence of said colored compound. In some embodiments, the enzyme is alkaline phosphatase. In some embodiments, the diazonium salt is 4-(benzoylamino)-2,5-diethoxybenzenediazo tetrachlorozincate (Fast Blue BB). In some embodiments, the target is selected from the group consisting of a nucleic acid and a protein. In some embodiments, the detection reagent comprises a first binding partner conjugated to said enzyme. In some embodiments, the first binding partner is selected from the group consisting of an antigen-binding protein, a nucleic acid, and a hapten. In some embodiments, the detection reagent comprises an enzyme conjugated to a nucleic acid, said target is a nucleic acid, and said detection reagent hybridizes to said target. In some embodiments, the detection reagent comprises an enzyme conjugated to an antigen-binding protein, said target is a protein, and said detection reagent binds to said analyte. In some embodiments, the detection is indirect and the detection reagent comprises an enzyme conjugated to an antigen-binding protein specific for a hapten. In some embodiments, the compound is as follows.

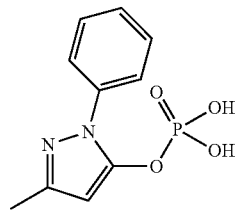 [SMILES: Cc1cc(OP(=O)(O)O)n(-c2ccccc2)n1]

The foregoing and other objects, features, and advantages of the invention will become more apparent from the following detailed description, which proceeds with reference to the accompanying figures.

DETAILED DESCRIPTION

Figure 1:
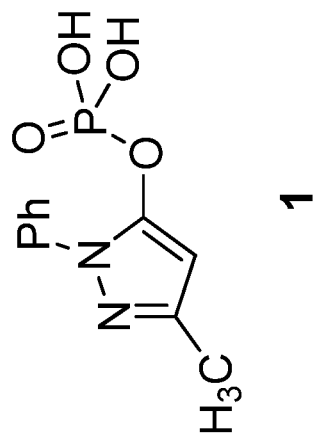
FIG. 1 is a chemical structure of an exemplary yellow/gold AP substrate 3-methyl-1-phenyl-1H-pyrazol-5-yl dihydrogen phosphate (1).
Figure 2:
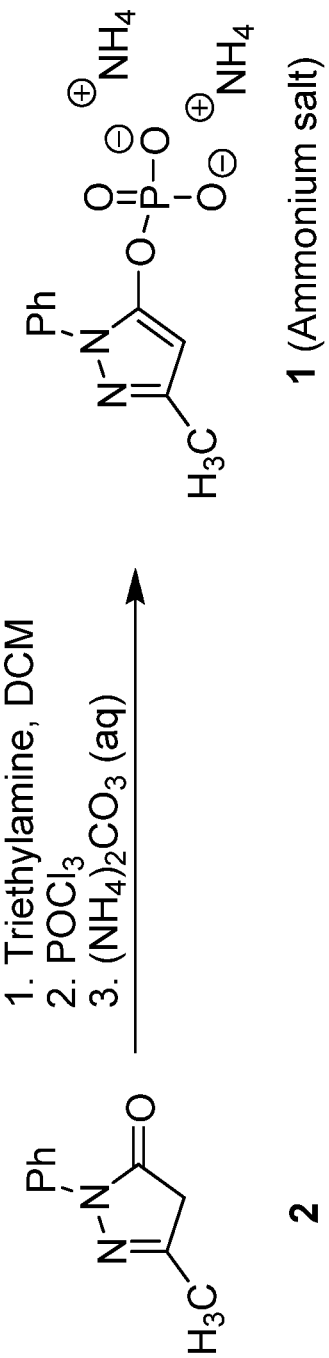
FIG. 2 is a scheme illustrating a synthetic route to the ammonium salt of 1.
Figure 3:
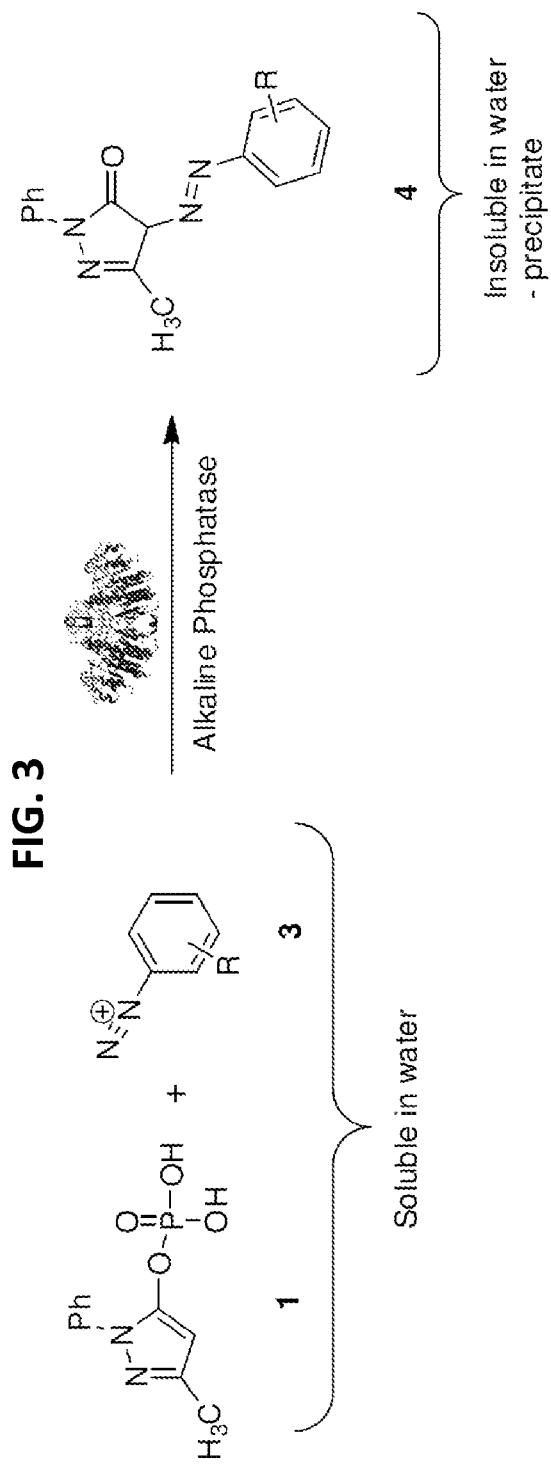
FIG. 3 is a schematic diagram of a reaction of AP substrate 1 with diazonium salts.

Disclosed herein are embodiments of substrates and processes for chromogenic detection, and in particular pyrazolyl dihydrogen phosphate compounds. Azo dyes comprising a pyrazole group such as tartrazine are well known. Some embodiments of the disclosed compounds are complimentary to the naphthol AS phosphate series and provide access to new detection colors. These compounds are preferably synthesized by trapping the enol tautomer of a pyrazole-5(4H)-one compound as the monophosphate ester. WO2007021966A1 describes pyrazole phosphate compounds; however, the 4 position of the pyrazole is substituted and unreactive to diazonium salts.

I. DEFINITIONS

Unless otherwise explained, all technical and scientific terms used herein have the same meaning as commonly understood by one of ordinary skill in the art to which this disclosure belongs. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" is used synonymously with the phrase "more than one," that is, two or more. It is further to be understood that all base sizes or amino acid sizes, and all molecular weight or molecular mass values, given for nucleic acids or polypeptides are approximate, and are provided for description. The term "comprises" means "includes." The abbreviation, "e.g.," is derived from the Latin exempli gratia, and is used herein to indicate a non-limiting example. Thus, the abbreviation "e.g.," is synonymous with the term "for example." Although methods and materials similar or equivalent to those described herein can be used in the practice or testing of this disclosure, suitable methods and materials are described below.

In order to facilitate review of the various embodiments of this disclosure, the following explanations of specific terms are provided:

Antibody: "Antibody" collectively refers to immunoglobulins or immunoglobulin-like molecules (including by way of example and without limitation, IgA, IgD, IgE, IgG and IgM, combinations thereof, and similar molecules produced during an immune response in any vertebrate, for example, in mammals such as humans, goats, rabbits and mice) and antibody fragments that specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4 M^{-1}$ greater or at least $10^5 M^{-1}$ greater than a binding constant for other molecules in a biological sample.

More particularly, "antibody" refers to a polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

This includes intact immunoglobulins and the variants and portions of them well known in the art. Antibody fragments include proteolytic antibody fragments [such as F(ab')$_2$ fragments, Fab' fragments, Fab'-SH fragments and Fab fragments as are known in the art], recombinant antibody fragments (such as sFv fragments, dsFv fragments, bispecific sFv fragments, bispecific dsFv fragments, F(ab)'$_2$ fragments, single chain Fv proteins ("scFv"), disulfide stabilized Fv proteins ("dsFv"), diabodies, and triabodies (as are known in the art), and camelid antibodies (see, for example, U.S. Pat. Nos. 6,015,695; 6,005,079-5,874,541; 5,840,526; 5,800,988; and 5,759,808). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook,* 1994-1995 (Pierce Chemical Co., Rockford, Ill.); Kuby, J., *Immunology,* 3.sup.rd Ed., W.H. Freeman & Co., New York, 1997.

Typically, a naturally occurring immunoglobulin has heavy (H) chains and light (L) chains interconnected by disulfide bonds. There are two types of light chain, lambda and kappa. There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest,* U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds RET will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

"Binding or stable binding" refers to the association between two substances or molecules, such as the hybridization of one nucleic acid molecule (e.g., a binding region) to another (or itself) (e.g., a target nucleic acid molecule). A nucleic acid molecule binds or stably binds to a target nucleic acid molecule if a sufficient amount of the nucleic acid molecule forms base pairs or is hybridized to its target nucleic acid molecule to permit detection of that binding.

A nucleic acid molecule is said to be "complementary" with another nucleic acid molecule if the two molecules share a sufficient number of complementary nucleotides to form a stable duplex or triplex when the strands bind (hybridize) to each other, for example by forming Watson-Crick, Hoogsteen or reverse Hoogsteen base pairs. Stable binding occurs when a nucleic acid molecule remains detectably bound to a target nucleic acid sequence (e.g., genomic target nucleic acid sequence) under the required conditions.

Complementarity is the degree to which bases in one nucleic acid molecule (e.g., target nucleic acid probe) base pair with the bases in a second nucleic acid molecule (e.g., genomic target nucleic acid sequence). Complementarity is conveniently described by percentage, that is, the proportion of nucleotides that form base pairs between two molecules or within a specific region or domain of two molecules.

In the present disclosure, "sufficient complementarity" means that a sufficient number of base pairs exist between one nucleic acid molecule or region thereof and a target nucleic acid sequence (e.g., genomic target nucleic acid sequence) to achieve detectable binding. A thorough treatment of the qualitative and quantitative considerations involved in establishing binding conditions is provided by Beltz et al. *Methods Enzymol.* 100:266-285, 1983, and by Sambrook et al. (ed.), *Molecular Cloning. A Laboratory Manual*, 2nd ed., vol. 1-3, Cold Spring Harbor Laboratory Press, Cold Spring Harbor, N.Y., 1989.

The terms "conjugating, joining, bonding or linking" refer to covalently linking one molecule to another molecule to make a larger molecule. For example, making two polypeptides into one contiguous polypeptide molecule, or to covalently attaching a hapten or other molecule to a polypeptide, such as an scFv antibody. In the specific context, the terms include reference to joining a specific binding molecule such as an antibody to a signal generating moiety, such as a quantum dot. The linkage can be either by chemical or recombinant means. "Chemical means" refers to a reaction between the antibody moiety and the effector molecule such that there is a covalent bond formed between the two molecules to form one molecule.

The term "coupled", when applied to a first atom or molecule being "coupled" to a second atom or molecule can be both directly coupled and indirectly coupled. A secondary antibody provides an example of indirect coupling. One specific example of indirect coupling is a rabbit anti-hapten primary antibody that is bound by a mouse anti-rabbit IgG antibody, that is in turn bound by a goat anti-mouse IgG antibody that is covalently linked to a detectable label.

The term "hapten" refers to a molecule, typically a small molecule that can combine specifically with an antibody, but typically is substantially incapable of being immunogenic except in combination with a carrier molecule.

A "label" is a detectable compound or composition that is conjugated directly or indirectly to another molecule to facilitate detection of that molecule. Specific, non-limiting examples of labels include fluorescent and fluorogenic moieties, chromogenic moieties, haptens, affinity tags, and radioactive isotopes. The label can be directly detectable (e.g., optically detectable) or indirectly detectable (for example, via interaction with one or more additional molecules that are in turn detectable). Exemplary labels in the context of the probes disclosed herein are described below. Methods for labeling nucleic acids, and guidance in the choice of labels useful for various purposes, are discussed, e.g., in Sambrook and Russell, in *Molecular Cloning: A Laboratory Manual*, 3rd Ed., Cold Spring Harbor Laboratory Press (2001) and Ausubel et al., in *Current Protocols in Molecular Biology*, Greene Publishing Associates and Wiley-Intersciences (1987, and including updates).

The term "multiplex" refers to embodiments that allow multiple targets in a sample to be detected substantially simultaneously, or sequentially, as desired, using plural different conjugates. Multiplexing can include identifying and/or quantifying nucleic acids generally, DNA, RNA, peptides, proteins, both individually and in any and all combinations. Multiplexing also can include detecting two or more of a gene, a messenger and a protein in a cell in its anatomic context.

A "nucleic acid" is a deoxyribonucleotide or ribonucleotide polymer in either single or double stranded form, and unless otherwise limited, encompasses analogues of natural nucleotides that hybridize to nucleic acids in a manner similar to naturally occurring nucleotides. The term "nucleotide" includes, but is not limited to, a monomer that includes a base (such as a pyrimidine, purine or synthetic analogs thereof) linked to a sugar (such as ribose, deoxyribose or synthetic analogs thereof), or a base linked to an amino acid, as in a peptide nucleic acid (PNA). A nucleotide is one monomer in a polynucleotide. A nucleotide sequence refers to the sequence of bases in a polynucleotide.

A "probe" or a "nucleic acid probe" is a nucleic acid molecule that is capable of hybridizing with a target nucleic acid molecule (e.g., genomic target nucleic acid molecule) and, when hybridized to the target, is capable of being detected either directly or indirectly. Thus probes permit the detection, and in some examples quantification, of a target nucleic acid molecule. In particular examples a probe includes a plurality of nucleic acid molecules, which include binding regions derived from the target nucleic acid molecule and are thus capable of specifically hybridizing to at least a portion of the target nucleic acid molecule. A probe can be referred to as a "labeled nucleic acid probe," indicating that the probe is coupled directly or indirectly to a detectable moiety or "label," which renders the probe detectable.

A "sample" is a biological specimen containing genomic DNA, RNA (including mRNA), protein, or combinations thereof, obtained from a subject. Examples include, but are not limited to, chromosomal preparations, peripheral blood, urine, saliva, tissue biopsy, surgical specimen, bone marrow, amniocentesis samples and autopsy material. In one example, a sample includes genomic DNA or RNA. In some examples, the sample is a cytogenetic preparation, for example which can be placed on microscope slides. In particular examples, samples are used directly, or can be manipulated prior to use, for example, by fixing (e.g., using formalin).

A "target nucleic acid sequence or molecule" is a defined region or particular sequence of a nucleic acid molecule, for example a genome (such as a gene or a region of mammalian genomic DNA containing a gene of interest) or an RNA sequence. In an example where the target nucleic acid sequence is a target genomic sequence, such a target can be defined by its position on a chromosome (e.g., in a normal cell), for example, according to cytogenetic nomenclature by reference to a particular location on a chromosome, by reference to its location on a genetic map, by reference to a hypothetical or assembled contig (i.e., a set of overlapping DNA segments derived from a single genetic source, by its specific sequence or function, by its gene or protein name, or by any other means that uniquely identifies it from among other genetic sequences of a genome. In some examples, the target nucleic acid sequence is mammalian or viral genomic sequence. In other examples, the target nucleic acid sequence is an RNA sequence.

In some examples, alterations of a target nucleic acid sequence (e.g., genomic nucleic acid sequence) are "associated with" a disease or condition. That is, detection of the target nucleic acid sequence can be used to infer the status of a sample with respect to the disease or condition. For example, the target nucleic acid sequence can exist in two (or more) distinguishable forms, such that a first form correlates with absence of a disease or condition and a second (or different) form correlates with the presence of the disease or condition. The two different forms can be qualitatively distinguishable, such as by polynucleotide polymorphisms, and/or the two different forms can be quantitatively distinguishable, such as by the number of copies of the target nucleic acid sequence that are present in a cell.

II. PYRAZOLYL DIHYDROGEN PHOSPHATE COMPOUNDS

The present disclosure is not limited to particular pyrazolyl dihydrogen phosphate compounds. In certain embodiments, the compounds are described by the following formula:

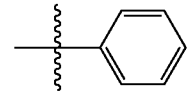

including salts and prodrugs thereof; and including both R and S enantiomeric forms and racemic mixtures thereof.

In some embodiments, $R^1$ is hydrogen, a halogen (e.g., chlorine, fluorine, bromine, iodine), a saturated or unsaturated aliphatic group of any desired length, or an aryl group of any desired size.

In some embodiments, $R^2$ is hydrogen, a saturated or unsaturated aliphatic group of any desired length, or an aryl group of any desired size.

In some embodiments, $R^1$ is hydrogen.
In some embodiments, $R^1$ is $CH_3$.
In some embodiments, $R^2$ is

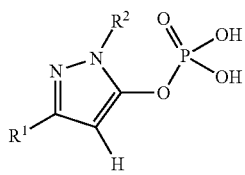

(phenyl).

In some embodiments, $R^2$ is hydrogen.

In some embodiments, the pyrazolyl dihydrogen phosphate compound is a salt that is further described by the following formula:

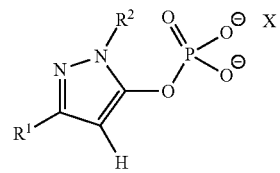

wherein X represents any ion having a positive charge.

In some embodiments, X is two of any monovalent positive ions (e.g., 2 $Na^+$, 2 $K^+$, 2 $NH_4^+$, etc.).

In some embodiments, X is any divalent positive ion (e.g., $Mg^{2+}$).

In some embodiments, the pyrazolyl dihydrogen phosphate compound is 3-methyl-1-phenyl-1H-pyrazol-5-yl dihydrogen phosphate:

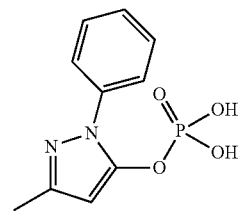 [SMILES: Cc1cc(OP(=O)(O)O)n(-c2ccccc2)n1]

including salts and prodrugs thereof; and including both R and S enantiomeric forms and racemic mixtures thereof.

III. APPLICATIONS

Some embodiments of the disclosed compounds are used in conjunction with a diazonium salt. It is contemplated that certain embodiments of the disclosed compounds are substrates for an enzyme, e.g., a hydrolase such as a phosphatase. It is further contemplated that in the presence of alkaline phosphatase and a diazonium salt, alkaline phosphatase catalytically cleaves the phosphates in the compounds, allowing the compounds to in turn react with the diazonium salt to produce a colored precipitate. In some embodiments, the diazonium salts include, but are not limited to, Fast Red KL (2-(aminocarbonyl)-5-methoxybenzene-diazonium), Fast Red B (2-methoxy-4-nitrobenzenediazonium), Diazo Red RC (5-chloro-2-methoxybenzenediazonium tetrachlorozincate), Variamine Blue RT (N-phenyl-p-phenylenediamine) and Fast Blue BB (4-(benzoylamino)-2,5-diethoxybenzenediazo tetrachlorozincate). In some embodiments, the colored precipitate is yellow or gold when viewed under standard brightfield microscopy conditions. In some embodiments, the diazonium salt is Fast Blue BB, which in the presence of some embodiments of the disclosed compounds and alkaline phosphatase, provides a colored precipitate which is gold or yellow when viewed under standard brightfield microscopy conditions.

Some embodiments of the disclosed compounds are useful for in situ hybridization procedures. In situ hybridization involves contacting a sample containing a target nucleic acid sequence (e.g., genomic target nucleic acid sequence) in the context of a metaphase or interphase chromosome preparation (such as a cell or tissue sample mounted on a slide) with a probe (i.e., the target nucleic acid probe described above) specifically hybridizable or specific for the target nucleic acid sequence (e.g., genomic target nucleic acid sequence). The slides are optionally pretreated, e.g., to remove paraffin or other materials present in formalin-fixed paraffin embedded tissues that can interfere with uniform hybridization. The chromosome sample and the probe are both treated, for example by heating, to denature the double stranded nucleic acids. The probe (formulated in a suitable hybridization buffer) and the sample are combined, under conditions and for sufficient time to permit hybridization to occur (typically to reach equilibrium). The chromosome preparation is washed to remove excess target nucleic acid probe, and detection of specific labeling of the chromosome target is performed. For a general description of in situ hybridization procedures, see, e.g., U.S. Pat. No. 4,888,278. Numerous procedures for fluorescence in situ hybridization (FISH), chromogenic in situ hybridization (CISH) and silver in situ hybridization (SISH) are known in the art. For example, procedures for performing FISH are described in U.S. Pat. Nos. 5,447,841, 5,472,842, 5,427,932, and for example, in Pinkel et al., *Proc. Natl. Acad. Sci.* 83:2934-2938, 1986; Pinkel et al., *Proc. Natl. Acad. Sci.* 85:9138-9142, 1988, and Lichter et al., *Proc. Natl. Acad. Sci.* 85:9664-9668, 1988. CISH is described in, e.g., Tanner et al., *Am. J. Pathol.* 157:1467-1472, 2000, and U.S. Pat. No. 6,942,970. Additional detection methods are provided in U.S. Pat. No. 6,280,929. Exemplary procedures for detecting viruses by in situ hybridization can be found in Poddighe et al., *J. Clin. Pathol.* 49:M340-M344, 1996.

In some embodiments, nucleic acid probes, which hybridize to one or more target nucleic acid sequences, are utilized. In direct detection embodiments, the nucleic acid probes may be conjugated to a suitable enzyme, for example, alkaline phosphatase. In indirect detection embodiments, the probes preferably comprise an accessory molecule, such as a hapten, which binds to a second reagent, such as an anti-hapten antibody.

The nucleic acid probes are capable of hybridizing to a target nucleic acid sequence under conditions suitable for hybridization, such as conditions suitable for in situ hybridization, Southern blotting, or Northern blotting. In some embodiments, the detection probe portion comprises any suitable nucleic acid, such as RNA, DNA, LNA, PNA or combinations thereof, and can comprise both standard nucleotides such as ribonucleotides and deoxyribonucleotides, as well as nucleotide analogs. LNA and PNA are two examples of nucleic acid analogs that form hybridization complexes that are more stable (i.e., have an increased $T_m$) than those formed between DNA and DNA or DNA and RNA. LNA and PNA analogs can be combined with traditional DNA and RNA nucleosides during chemical synthesis to provide hybrid nucleic acid molecules that can be used as probes. Use of the LNA and PNA analogs allows modification of hybridization parameters such as the $T_m$ of the hybridization complex. This allows the design of detection probes that hybridize to the detection target sequences of the target nucleic acid probes under conditions that are the same or similar to the conditions required for hybridization of the target probe portion to the target nucleic acid sequence.

Suitable nucleic acid probes can be selected manually, or with the assistance of a computer-implemented algorithm that optimizes probe selection based on desired parameters, such as temperature, length, GC content, etc. Numerous computer-implemented algorithms or programs for use via the internet or on a personal computer are available. For example, to generate multiple binding regions from a target nucleic acid sequence (e.g., genomic target nucleic acid sequence), regions of sequence devoid of repetitive (or other undesirable, e.g., background-producing) nucleic acid sequence are identified, for example manually or by using a computer algorithm, such as RepeatMasker. Methods of creating repeat-depleted and uniquely specific probes are found in, for example, US Patent Application Publication Nos. 2001/0051342 and 2008/0057513 and U.S. Provisional Patent Application Ser. Nos. 61/291,750 and 61/314,654. Within a target nucleic acid sequence (e.g., genomic target nucleic acid sequence) that spans several to several-hundred kilobases, typically numerous binding regions that are substantially or preferably completely free of repetitive (or other undesirable, e.g., background-producing) nucleic acid sequences are identified.

In some embodiments, a hapten is incorporated into a nucleic acid probe, for example, by use of a haptenylated nucleoside. Methods for conjugating haptens and other labels to dNTPs (e.g., to facilitate incorporation into labeled probes) are well known in the art. For examples of procedures, see, e.g., U.S. Pat. Nos. 5,258,507, 4,772,691, 5,328,824, and 4,711,955. Indeed, numerous labeled dNTPs are available commercially, for example from Invitrogen Detection Technologies (Molecular Probes, Eugene, Oreg.). A label can be directly or indirectly attached to a dNTP at any location on the dNTP, such as a phosphate (e.g., α, β or γ phosphate) or a sugar. The probes can be synthesized by any suitable nucleic acid synthesis method. In some embodiments, the detection probes are chemically synthesized using phosphoramidite nucleosides and/or phosphoramidite nucleoside analogs. For example, in some embodiments, the probes are synthesized by using standard RNA or DNA phosphoramidite nucleosides. In some embodiments, the probes are synthesized using either LNA phosphoramidites or PNA phosphoramidites, alone or in combination with standard phosphoramidite nucleosides. In some embodiments, haptens are introduced on abasic phosphoramidites containing the desired detectable moieties. Other methods can also be used for detection probe synthesis. For example, a primer made from LNA analogs or a combination of LNA analogs and standard nucleotides can be used for transcription of the remainder of the probe. As another example, a primer comprising detectable moieties is utilized for transcription of the rest of the probe. In still other embodiments, segments of the probe produced, for example, by transcription or chemical synthesis, may be joined by enzymatic or chemical ligation.

A variety of haptens may be used in the detectable moiety portion of the detection probe. Such haptens include, but are not limited to, pyrazoles, particularly nitropyrazoles; nitrophenyl compounds; benzofurazans; triterpenes; ureas and thioureas, particularly phenyl ureas, and even more particularly phenyl thioureas; rotenone and rotenone derivatives, also referred to herein as rotenoids; oxazole and thiazoles, particularly oxazole and thiazole sulfonamides; coumarin and coumarin derivatives; cyclolignans, exemplified by podophyllotoxin and podophyllotoxin derivatives; and combinations thereof. Specific examples of haptens include, but are not limited to, 2,4-dinitrophenyl (DNP), biotin, fluorescein derivatives (FITC, TAMRA, Texas Red, etc.), digoxigenin (DIG), 5-nitro-3-pyrazolecarbamide (nitropyrazole, NP), 4,5,-dimethoxy-2-nitrocinnamide (nitrocinnamide, NCA), 2-(3,4-dimethoxyphenyl)-quinoline-4-carbamide (phenylquinolone, DPQ), 2,1,3-benzoxadiazole-5-carbamide (benzofurazan, BF), 3-hydroxy-2-quinoxalinecarbamide (hydroxyquinoxaline, HQ), 4-(dimethylamino)azobenzene-4'-sulfonamide (DABSYL), rotenone isoxazoline (Rot), (E)-2-(2-(2-oxo-2,3-dihydro-1H-benzo[b][1,4]diazepin-4-yl)phenozy)acetamide (benzodiazepine, BD), 7-(diethylamino)-2-oxo-2H-chromene-3-carboxylic acid (coumarin 343, DCC), 2-acetamido-4-methyl-5-thiazolesulfonamide (thiazolesulfonamide, TS), and p-methoxyphenylpyrazopodophyllamide (Podo). These haptens and their use in probes are described in more detail in co-owned U.S. Pat. No. 7,695,929 and US Pat. Publ. Nos. 2008/0305497, and 2008/0057513, incorporated herein by reference in their entireties.

Haptenylated probes are preferably detected by use of an anti-hapten antigen-binding protein. In some embodiments, the anti-hapten antigen-binding proteins are conjugated to an enzyme, for example, alkaline phosphatase. Examples of suitable antigen-binding molecules include, but are not limited to, antibodies, immunoglobulins or immunoglobulin-like molecules (including by way of example and without limitation, IgA, IgD, IgE, IgG and IgM), antibody fragments such as F(ab')$_2$ fragments, Fab' fragments, Fab'-SH fragments and Fab fragments as are known in the art, recombinant antibody fragments (such as sFv fragments, dsFv fragments, bispecific sFv fragments, bispecific dsFv fragments, F(ab)'$_2$ fragments, single chain Fv proteins ("scFv"), disulfide stabilized Fv proteins ("dsFv"), diabodies, and triabodies (as are known in the art), and camelid antibodies (see, for example, U.S. Pat. Nos. 6,015,695; 6,005,079-5,874,541; 5,840,526; 5,800,988; and 5,759,808). Examples of suitable conjugates include, but are not limited to anti-DNP, anti-biotin, anti-FITC, anti-DIG, anti-NP, anti-NCA, anti-DPQ, anti-BF, anti-HQ, anti-DABSYL, anti-Rot, anti-BD, anti-DCC, anti-TS, and anti-Podo antibodies that are conjugated to an enzyme that reacts with embodiments of the disclosed compounds. In further embodiments, the anti-hapten antibody may be a first antibody that is not conjugated to an enzyme. In these embodiments, a secondary anti-antibody (such as a goat anti-mouse IgG antibody) that comprises an enzyme is utilized for generating a detectable signal.

Some embodiments of the disclosed compounds are useful in immunohistochemistry procedures. Immunohistochemistry (IHC) is the localization of antigens or proteins in tissue sections by the use of labeled antibodies as specific reagents through antigen-antibody interactions that are visualized by a marker such as a fluorescent compound (e.g., a fluorophore, a quantum dot, a fluorescent particle, etc.), an enzyme (e.g., in conjunction with substrates and chromogens for chromogenic deposition), colloidal gold, or a mass tag. For example, a primary antibody binds a specific antigen; the antibody-antigen complex is bound by a secondary, enzyme-conjugated, antibody; and in the presence of substrate and chromogen, the enzyme forms a colored deposit at the sites of antibody-antigen binding. Suitable methods for IHC are known in the art.

In some direct detection embodiments, the enzyme is conjugated to a first binding partner selected from an antigen-binding protein, a nucleic acid, and a hapten. In some embodiments, the first binding partner is an antigen-binding protein, such as an antibody, that is specific for a target peptide. In some indirect detection embodiments, a first antibody is used that binds to a target peptide. The first antibody is then detected with a second antibody that is conjugated to the enzyme. In some indirect detection embodiments, the first antibody comprises a hapten and the enzyme is conjugated to an anti-hapten antibody. In these embodiments, the anti-hapten antibody binds to the haptenylated first antibody. In other indirect detection embodiments, additional antibodies are used. For example, in some embodiments, the second antibody is a rabbit, mouse or goat anti-hapten antibody and the third antibody is an enzyme-conjugated anti-rabbit, anti-mouse, or anti-goat antibody, respectively. Examples of suitable linker and attachment chemistries are described in U.S. Patent Application Publication Nos. 2006/0246524; 2006/0246523, and U.S. Provisional Patent Application No. 60/739,794. Antigen-binding proteins are not limited to antibodies. Any suitable antigen-binding protein may be utilized. Examples of suitable antigen-binding molecules include, but are not limited to, antibodies, immunoglobulins or immunoglobulin-like molecules (including by way of example and without limitation, IgA, IgD, IgE, IgG and IgM), antibody fragments such as F(ab')$_2$ fragments, Fab' fragments, Fab'-SH fragments and Fab fragments as are known in the art, recombinant antibody fragments (such as sFv fragments, dsFv fragments, bispecific sFv fragments, bispecific dsFv fragments, F(ab)'$_2$ fragments, single chain Fv proteins ("scFv"), disulfide stabilized Fv proteins ("dsFv"), diabodies, and triabodies (as are known in the art), and camelid antibodies (see, for example, U.S. Pat. Nos. 6,015,695; 6,005,079; 5,874,541; 5,840,526; 5,800,988; and 5,759,808).

Some embodiments of the disclosed compounds are used in conjunction with other detection technologies, including, but not limited to, fluorescent label detection, quantum dot detection, metal sols, mass tags and similar technologies. In some embodiments, the compounds are used in conjunction with other chromogen substrates and/or enzymes in multicolor applications. Examples of suitable enzymes include, but are not limited to, phosphatases such as alkaline phosphatase and acid phosphatase. Particular examples of enzyme substrates and enzyme substrate systems useful in chromogenic detection assays include, but are not limited to, naphthol phosphate, naphthol phosphate/Fast Red (and variations thereof such as Fast Red TR/Naphthol AS, naphthol phosphate/fuschin, Fast Blue BB (4-(benzoylamino)-2,5-diethoxybenzenediazotetrachlorozincate), bromochloroindolyl phosphate (BCIP), BCIP/NBT, and BCIP/INT.

IV. KITS

Embodiments of kits for detection of a target in a biological sample are disclosed. In some embodiments, the kits comprise at least one embodiment of a pyrazolyl dihydrogen phosphate compound as disclosed herein and a suitable diazonium salt. In some embodiments, the kits further comprise one or more detection reagents for target detection. In some embodiments, the detection reagent is a nucleic acid conjugated to an enzyme, such as alkaline phosphatase. In some embodiments, the detection reagent comprises an enzyme, such as alkaline phosphatase, conjugated to an antigen-binding protein specific for a target peptide. In some embodiments, the detection reagents allow indirect detection of a target. For example, in some embodiments, the detection reagents comprise a haptenylated nucleic acid probe and an anti-hapten antibody conjugated to an enzyme such as alkaline phosphatase. In some embodiments, the kits comprise a haptenylated first antibody specific for a target and an anti-hapten antibody conjugated to an enzyme such as alkaline phosphatase. In other embodiments, the kits comprise a haptenylated first antibody specific for a target, an anti-hapten second antibody specific for the hapten, and a third antibody conjugated to an enzyme such as alkaline phosphatase, wherein the third antibody is specific for the second antibody (e.g., the second antibody is a goat antibody and the third antibody is an anti-goat antibody). Other combinations for indirect detection will be apparent to those of skill in the art. In some embodiments, the kits comprise a combination of detection reagents such that more than one target can be detected on a sample (e.g., for multiplex detection of one or more target molecules that may be present in a tissue).

V. TARGETS AND PROBES

A target nucleic acid molecule can be any selected nucleic acid, such as DNA or RNA. In some embodiments, the target nucleic acid is detected in a cell fixed on a slide. In some embodiments, the target nucleic acid is detected in a tissue fixed on a slide.

In particular embodiments, the target sequence is a genomic target sequence or genomic subsequence, for example from a eukaryotic genome, such as a human genome. In some embodiments, the target nucleic acid is cytoplasmic RNA. In some embodiments, the target nucleic acid molecule is selected from a pathogen, such as a virus, bacteria, or intracellular parasite, such as from a viral genome. In some embodiments, the target nucleic acid sequence is a genomic sequence, such as eukaryotic (e.g., mammalian) or viral genomic sequence. Target nucleic acid probes can be generated which correspond to essentially any genomic target sequence that includes at least a portion of unique non-repetitive DNA. For example, the genomic target sequence can be a portion of a eukaryotic genome, such as a mammalian (e.g., human), fungal or intracellular parasite genome. Alternatively, a genomic target sequence can be a viral or prokaryotic genome (such as a bacterial genome), or portion thereof. In a specific example, the genomic target sequence is associated with an infectious organism (e.g., virus, bacteria, fungi).

In some embodiments, the target nucleic acid molecule comprises a sequence associated with (e.g., correlated with, causally implicated in, etc.) a disease. In some embodiments, a target sequence is selected that is associated with a disease or condition, such that detection of hybridization can be used to infer information (such as diagnostic or prognostic information for the subject from whom the sample is obtained) relating to the disease or condition. In certain embodiments, the selected target nucleic acid molecule is a target nucleic acid molecule associated with a neoplastic disease (or cancer). In some embodiments, the genomic target sequence includes at least one gene associated with cancer (e.g., HER2, c-Myc, n-Myc, Abl, Bcl2, Bcl6, R1, p53, EGFR, TOP2A, MET, IGF1R) or genes encoding other receptors and/or signaling molecules, etc., or a chromosomal region associated with a cancer. In some embodiments, the target nucleic acid sequence is associated with a chromosomal structural abnormality, e.g., a translocation, deletion, or reduplication (e.g., gene amplification or polysomy) that has been correlated with a cancer. In some embodiments, the target nucleic acid sequence encompasses a genomic sequence that is reduplicated or deleted in at least some neoplastic cells.

The target nucleic acid sequence (e.g., genomic target nucleic acid sequence) can span any number of base pairs. In some embodiments, the target nucleic acid sequence spans at least 1000 base pairs. In some embodiments, the target nucleic acid sequence is at least 20 base pairs in length, at least 100 base pairs in length, at least 1000 base pairs in length, at least 50,000, at least 100,000, or even at least 250,000 base pairs in overall length. In specific examples, a target nucleic acid sequence (e.g., a genomic target nucleic acid sequence) is at least 10,000, at least 50,000, at least 100,000, at least 150,000, at least 250,000, or at least 500,000 base pairs in length (such as 100 kb to 600 kb, 200 kb to 500 kb, or 300 kb to 500 kb). In examples, where the target nucleic acid sequence is from a eukaryotic genome (such as a mammalian genome, e.g., a human genome), the target sequence typically represents a small portion of the genome (or a small portion of a single chromosome) of the organism (for example, less than 20%, less than 10%, less than 5%, less than 2%, or less than 1% of the genomic DNA (or a single chromosome) of the organism). In some examples where the target sequence (e.g., genomic target nucleic acid sequence) is from an infectious organism (such as a virus), the target sequence can represent a larger proportion (for example, 50% or more) or even all of the genome of the infectious organism.

In specific non-limiting examples, a target nucleic acid sequence (e.g., a genomic target nucleic acid sequence) associated with a neoplasm (for example, a cancer) is selected. Numerous chromosome abnormalities (including translocations and other rearrangements, reduplication or deletion) have been identified in neoplastic cells, especially in cancer cells, such as B cell and T cell leukemias, lymphomas, breast cancer, colon cancer, gastric cancer, esophageal cancer, lung cancer (e.g., non-small cell lung cancer, small cell lung cancer), neurological cancers and the like. Therefore, in some examples, at least a portion of the target nucleic acid sequence (e.g., genomic target nucleic acid sequence) is reduplicated or deleted in at least a subset of cells in a sample.

Translocations involving oncogenes are known for several human malignancies. For example, chromosomal rearrangements involving the SYT gene located in the breakpoint region of chromosome 18q11.2 are common among synovial sarcoma soft tissue tumors. The t(18q11.2) translocation can be identified, for example, using probes with different labels: the first probe includes nucleic acid molecules generated from a target nucleic acid sequence that extends distally from the SYT gene, and the second probe includes nucleic acid generated from a target nucleic acid sequence that extends 3' or proximal to the SYT gene. When probes corresponding to these target nucleic acid sequences (e.g., genomic target nucleic acid sequences) are used in an in situ hybridization procedure, normal cells, which lack a t(18q11.2) in the SYT gene region, exhibit two fusion (generated by the two labels in close proximity) signals, reflecting the two intact copies of SYT. Abnormal cells with a t(18q11.2) exhibit a single fusion signal.

Numerous examples of reduplication of genes involved in neoplastic transformation have been observed, and can be detected cytogenetically by in situ hybridization using the disclosed probes. In one example, the target nucleic acid sequence (e.g., a genomic target nucleic acid sequence) includes a gene (e.g., an oncogene) that is reduplicated in one or more malignancies (e.g., a human malignancy). For example, HER2, also known as c-erbB2 or HER2/neu, is a gene that plays a role in the regulation of cell growth (a representative human HER2 genomic sequence is provided at GENBANK™ Accession No. NC_000017, nucleotides 35097919-35138441). The HER2 gene codes for a 185 kd transmembrane cell surface receptor that is a member of the tyrosine kinase family. HER2 is amplified in human breast, ovarian, gastric and other cancers. Therefore, a HER2 gene (or a region of chromosome 17 that includes the HER2 gene) can be used as a genomic target nucleic acid sequence to generate probes that include nucleic acid molecules with binding regions specific for HER2.

In other examples, the target nucleic acid sequence (e.g., a genomic target nucleic acid sequence) is a tumor suppressor gene that is deleted (lost) in malignant cells. For example, the p16 region (including D9S1749, D9S1747, p16(INK4A), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

Accordingly, in some embodiments, "break-apart" probe sets are provided. In some embodiments, the break-apart probe sets comprise a first probe that hybridizes to one side of a known breakpoint for a chromosomal translocation and a second probe that hybridizes to the other side of the known breakpoint. Different chromogenic detection reagents are utilized for each of the probes of the break-apart probe set so that translocations can be detected. Examples of break-apart probe sets include, but are not limited to, sets for mucosa-associated lymphoid tissue (MALT), anaplastic lymphoid kinase (ALK), ETS-related gene (ERG) and androgen-related rearrangement partners like TMPRSS2 (androgen-regulated, prostate-specific serine 2 protease) suggestive of prostate cancer.

The aforementioned examples are provided solely for purpose of illustration and are not intended to be limiting. Numerous other cytogenetic abnormalities that correlate with neoplastic transformation and/or growth are known to those of skill in the art. Target nucleic acid sequences (e.g., genomic target nucleic acid sequences), which have been correlated with neoplastic transformation and which are useful in the disclosed methods and for which disclosed probes can be prepared, also include the EGFR gene (7p12; e.g., GENBANK™ Accession No. NC_000007, nucleotides 55054219-55242525), the C-MYC gene (8q24.21; e.g., GENBANK™ Accession No. NC_000008, nucleotides 128817498-128822856), D5S271 (5p15.2), lipoprotein lipase (LPL) gene (8p22; e.g., GENBANK™ Accession No. NC_000008, nucleotides 19841058-19869049), RB1 (13q14; e.g., GENBANK™ Accession No. NC_000013, nucleotides 47775912-47954023), p53 (17p13.1; e.g., GENBANK™ Accession No. NC_000017, complement, nucleotides 7512464-7531642)), N-MYC (2p24; e.g., GENBANK™ Accession No. NC_000002, complement, nucleotides 151835231-151854620), CHOP (12q13; e.g., GENBANK™ Accession No. NC_000012, complement, nucleotides 56196638-56200567), FUS (16p11.2; e.g., GENBANK™ Accession No. NC_000016, nucleotides 31098954-31110601), FKHR (13p14; e.g., GENBANK™ Accession No. NC_000013, complement, nucleotides 40027817-40138734), as well as, for example: ALK (2p23; e.g., GENBANK™ Accession No. NC_000002, complement, nucleotides 29269144-29997936), Ig heavy chain, CCND1 (11q13; e.g., GENBANK™ Accession No. NC_000011, nucleotides 69165054 . . . 69178423), BCL2 (18q21.3; e.g., GENBANK™ Accession No. NC_000018, complement, nucleotides 58941559-59137593), BCL6 (3q27; e.g., GENBANK™ Accession No. NC_000003, complement, nucleotides 188921859-188946169), MALF1, AP1 (1p32-p31; e.g., GENBANK™ Accession No. NC_000001, complement, nucleotides 59019051-59022373), TOP2A (17q21-q22; e.g., GENBANK™ Accession No. NC_000017, complement, nucleotides 35798321-35827695), TMPRSS (21q22.3; e.g., GENBANK™ Accession No. NC_000021, complement, nucleotides 41758351-41801948), ERG (21q22.3; e.g., GENBANK™ Accession No. NC_000021, complement, nucleotides 38675671-38955488); ETV1 (7p21.3; e.g., GENBANK™ Accession No. NC_000007, complement, nucleotides 13897379-13995289), EWS (22q12.2; e.g., GENBANK™ Accession No. NC_000022, nucleotides 27994271-28026505); FLI1 (11q24.1-q24.3; e.g., GENBANK™ Accession No. NC_000011, nucleotides 128069199-128187521), PAX3 (2q35-q37; e.g., GENBANK™ Accession No. NC_000002, complement, nucleotides 222772851-222871944), PAX7 (1p36.2-p36.12; e.g., GENBANK™ Accession No. NC_000001, nucleotides 18830087-18935219, PTEN (10q23.3; e.g., GENBANK™ Accession No. NC_000010, nucleotides 89613175-89716382), AKT2 (19q13.1-q13.2; e.g., GENBANK™ Accession No. NC_000019, complement, nucleotides 45431556-45483036), MYCL1 (1p34.2; e.g., GENBANK™ Accession No. NC_000001, complement, nucleotides 40133685-40140274), REL (2p13-p12; e.g., GENBANK™ Accession No. NC_000002, nucleotides 60962256-61003682) and CSF1R (5q33-q35; e.g., GENBANK™ Accession No. NC_000005, complement, nucleotides 149413051-149473128). A disclosed target nucleic acid probe or method may include a region of the respective human chromosome containing at least any one (or more, as applicable) of the foregoing genes. For example, the target nucleic acid sequence for some disclosed probes or methods includes any one of the foregoing genes and sufficient additional contiguous genomic sequence (whether 5' of the gene, 3' of the gene, or a combination thereof) for a total of at least 100,000 base pairs (such as at least 250,000, or at least 500,000 base pairs) or a total of between 100,000 and 500,000 base pairs.

In certain embodiments, the probe specific for the target nucleic acid molecule is assayed (in the same or a different but analogous sample) in combination with a second probe that provides an indication of chromosome number, such as a chromosome-specific (e.g., centromere) probe. For example, a probe specific for a region of chromosome 17 containing at least the HER2 gene (a HER2 probe) can be used in combination with a chromosome 17 (CEP 17) probe that hybridizes to the alpha satellite DNA located at the centromere of chromosome 17 (17p11.1-q11.1). Inclusion of the CEP 17 probe allows for the relative copy number of the HER2 gene to be determined. For example, normal samples will have a HER2/CEP17 ratio of less than 2, whereas samples in which the HER2 gene is reduplicated will have a HER2/CEP17 ratio of greater than 2.0. Similarly, CEP centromere probes corresponding to the location of any other selected genomic target sequence can also be used in combination with a probe for a unique target on the same (or a different) chromosome.

In other examples, a target nucleic acid sequence (e.g., genomic target nucleic acid sequence) is selected from a virus or other microorganism associated with a disease or condition. Detection of the virus- or microorganism-derived target nucleic acid sequence (e.g., genomic target nucleic acid sequence) in a cell or tissue sample is indicative of the presence of the organism. For example, the probe can be selected from the genome of an oncogenic or pathogenic virus, a bacterium or an intracellular parasite (such as *Plasmodium falciparum* and other *Plasmodium* species, *Leishmania* (sp.),

*Cryptosporidium parvum, Entamoeba histolytica,* and *Giardia lamblia,* as well as *Toxoplasma, Eimeria, Theileria,* and *Babesia* species).

In some examples, the target nucleic acid sequence (e.g., a genomic target nucleic acid sequence) is a viral genome. Exemplary viruses and corresponding genomic sequences (GENBANK™ RefSeq Accession No. in parentheses) include human adenovirus A (NC_001460), human adenovirus B (NC_004001), human adenovirus C(NC_001405), human adenovirus D (NC_002067), human adenovirus E (NC_003266), human adenovirus F (NC_001454), human astrovirus (NC_001943), human BK polyomavirus (V01109; GI:60851) human bocavirus (NC_007455), human coronavirus 229E (NC_002645), human coronavirus HKU1 (NC_006577), human coronavirus NL63 (NC_005831), human coronavirus OC43 (NC_005147), human enterovirus A (NC_001612), human enterovirus B (NC_001472), human enterovirus C (NC_001428), human enterovirus D (NC_001430), human erythrovirus V9 (NC_004295), human foamy virus (NC_001736), human herpesvirus 1 (Herpes simplex virus type 1) (NC_001806), human herpesvirus 2 (Herpes simplex virus type 2) (NC_001798), human herpesvirus 3 (Varicella zoster virus) (NC_001348), human herpesvirus 4 type 1 (Epstein-Barr virus type 1) (NC_007605), human herpesvirus 4 type 2 (Epstein-Barr virus type 2) (NC_009334), human herpesvirus 5 strain AD169 (NC_001347), human herpesvirus 5 strain Merlin Strain (NC_006273), human herpesvirus 6A (NC_001664), human herpesvirus 6B (NC_000898), human herpesvirus 7 (NC_001716), human herpesvirus 8 type M (NC_003409), human herpesvirus 8 type P (NC_009333), human immunodeficiency virus 1 (NC_001802), human immunodeficiency virus 2 (NC_001722), human metapneumovirus (NC_004148), human papillomavirus-1 (NC_001356), human papillomavirus-18 (NC_001357), human papillomavirus-2 (NC_001352), human papillomavirus-54 (NC_001676), human papillomavirus-61 (NC_001694), human papillomavirus-cand90 (NC_004104), human papillomavirus RTRX7 (NC_004761), human papillomavirus type 10 (NC_001576), human papillomavirus type 101 (NC_008189), human papillomavirus type 103 (NC_008188), human papillomavirus type 107 (NC_009239), human papillomavirus type 16 (NC_001526), human papillomavirus type 24 (NC_001683), human papillomavirus type 26 (NC_001583), human papillomavirus type 32 (NC_001586), human papillomavirus type 34 (NC_001587), human papillomavirus type 4 (NC_001457), human papillomavirus type 41 (NC_001354), human papillomavirus type 48 (NC_001690), human papillomavirus type 49 (NC_001591), human papillomavirus type 5 (NC_001531), human papillomavirus type 50 (NC_001691), human papillomavirus type 53 (NC_001593), human papillomavirus type 60 (NC_001693), human papillomavirus type 63 (NC_001458), human papillomavirus type 6b (NC_001355), human papillomavirus type 7 (NC_001595), human papillomavirus type 71 (NC_002644), human papillomavirus type 9 (NC_001596), human papillomavirus type 92 (NC_004500), human papillomavirus type 96 (NC_005134), human parainfluenza virus 1 (NC_003461), human parainfluenza virus 2 (NC_003443), human parainfluenza virus 3 (NC_001796), human parechovirus (NC_001897), human parvovirus 4 (NC_007018), human parvovirus B19 (NC_000883), human respiratory syncytial virus (NC_001781), human rhinovirus A (NC_001617), human rhinovirus B (NC_001490), human spumaretrovirus (NC_001795), human T-lymphotropic virus 1 (NC_001436), human T-lymphotropic virus 2 (NC_001488).

In certain examples, the target nucleic acid sequence (e.g., genomic target nucleic acid sequence) is from an oncogenic virus, such as Epstein-Barr Virus (EBV) or a human papilloma virus (HPV, e.g., HPV16, HPV18). In other examples, the target nucleic acid sequence (e.g., genomic target nucleic acid sequence) is from a pathogenic virus, such as a respiratory syncytial virus, a hepatitis virus (e.g., hepatitis C virus), a coronavirus (e.g., SARS virus), an adenovirus, a polyomavirus, a cytomegalovirus (CMV), or a herpes simplex virus (HSV).

V. EXAMPLES

Example 1

Synthesis of 3-methyl-1-phenyl-1H-pyrazol-5-yl phosphate, bis-triethylamine salt (1)

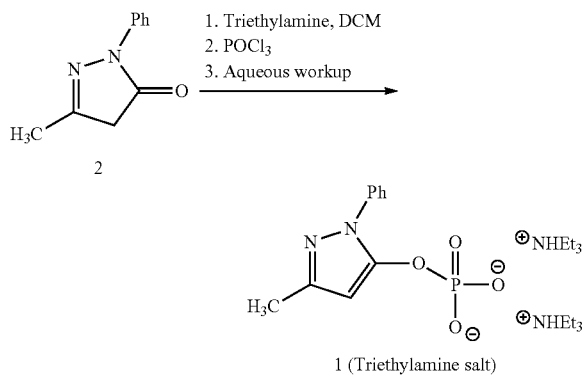

Figure 10:
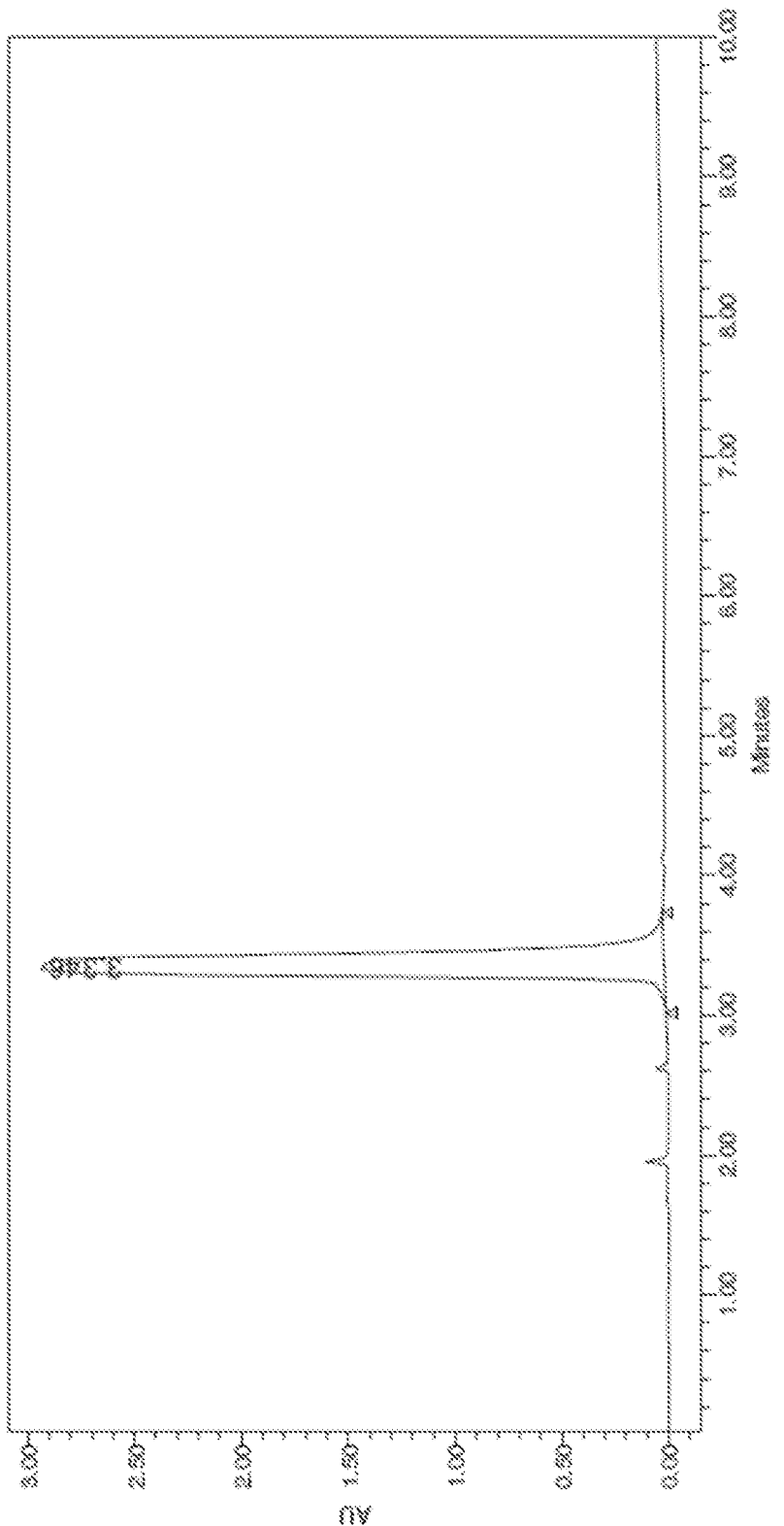
FIG. 10 is an HPLC trace of purified compound 1.
Figure 11:
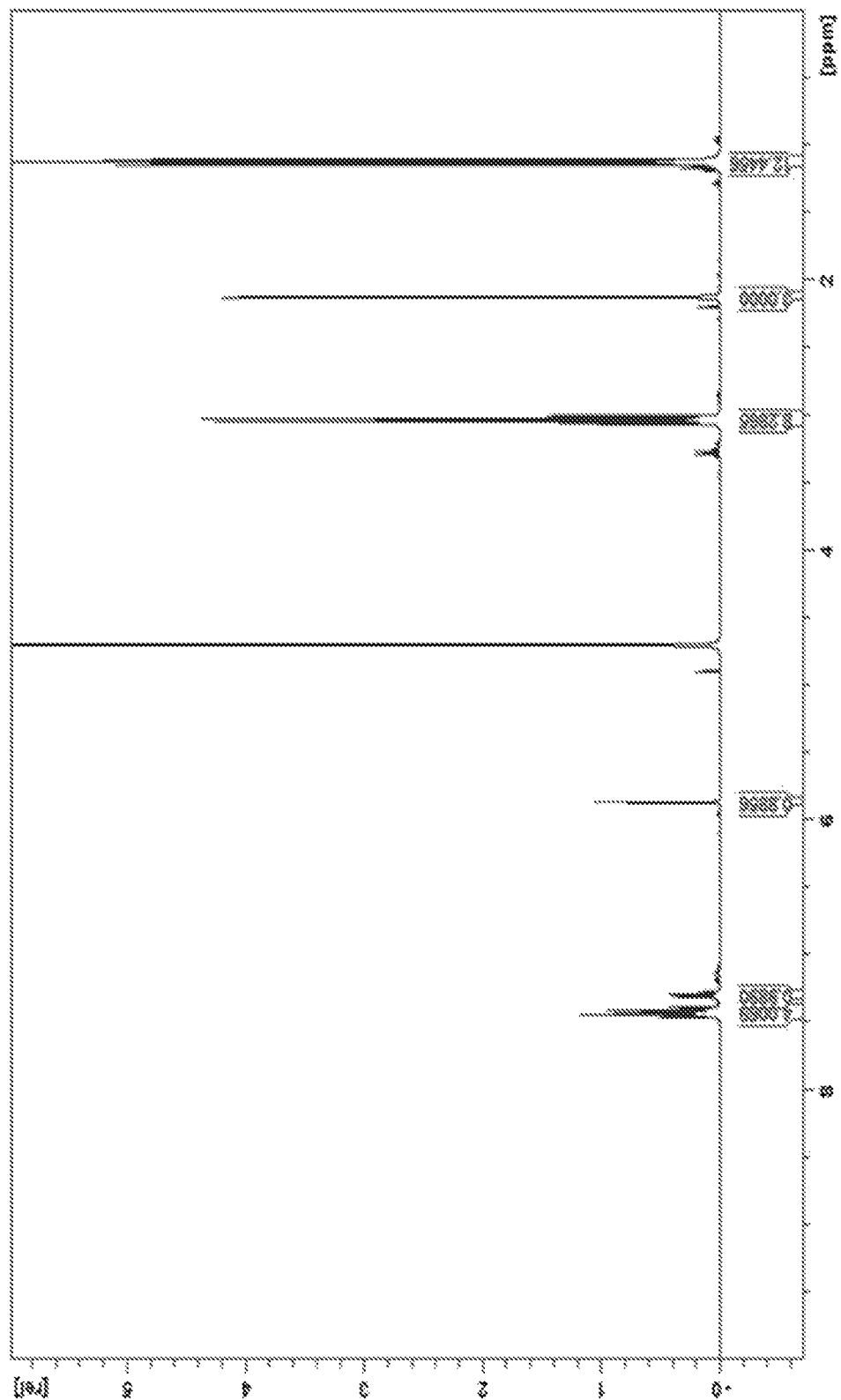
FIG. 11 is a representative $^1$H nuclear magnetic resonance trace of 3-methyl-1-phenyl-1H-pyrazol-5-yl phosphate, bis-triethylamine salt (1) in $D_2O$.
Figure 12:
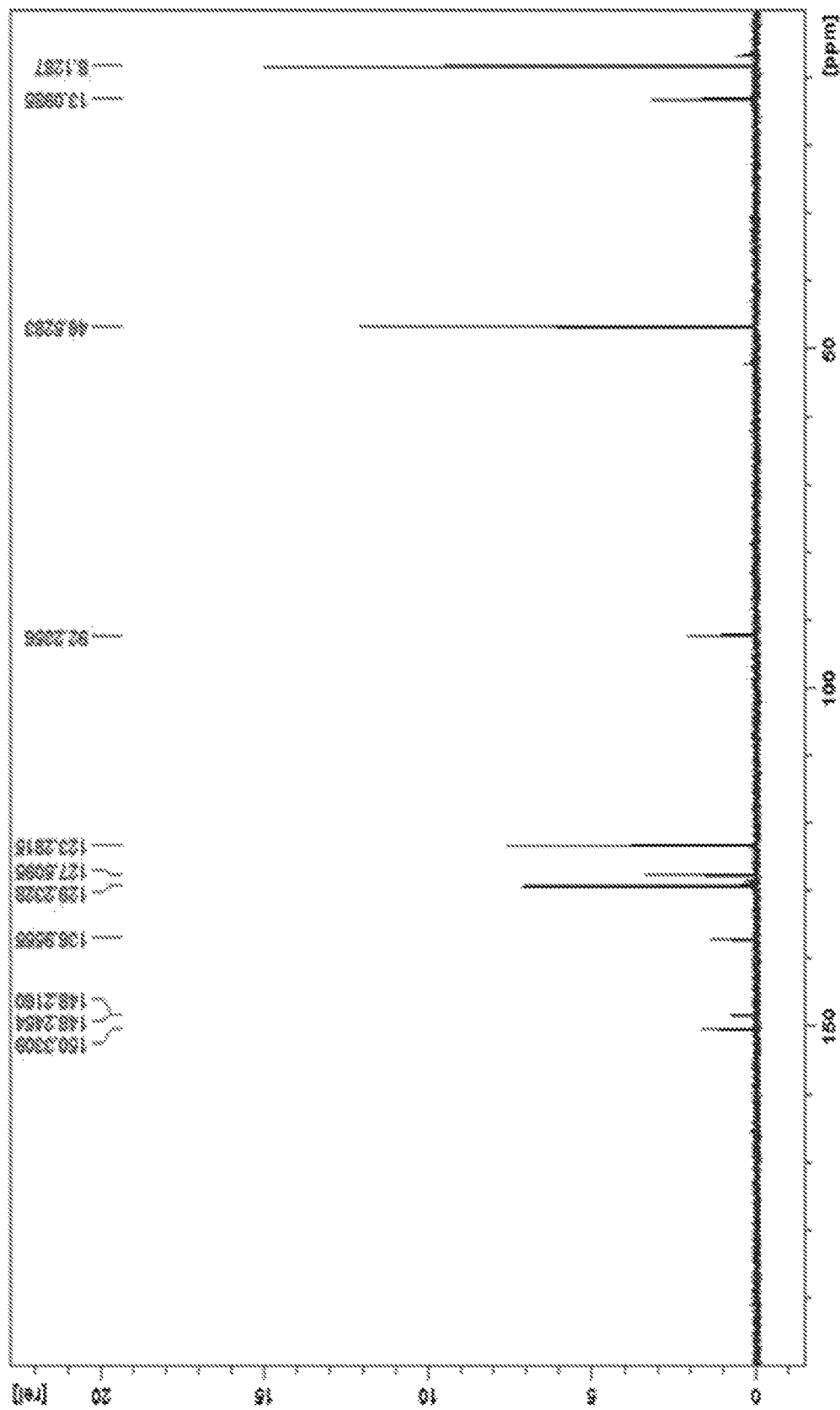
FIG. 12 is a representative $^{13}$C nuclear magnetic resonance trace of 3-methyl-1-phenyl-1H-pyrazol-5-yl phosphate, bis-triethylamine salt (1) in $D_2O$.

A 100 mL round bottom flask with a stir bar, addition funnel and septum was charged with 1.05 mL of phosphorus oxychloride (11.5 mmol, 2.0 equiv, Fluka 79580) and 5 mL of dichloromethane (Sigma). The flask was purged with nitrogen. In a separate vessel, 1.0 g of 3-methyl-1-phenyl-pyrazoline-5-one (2) (5.7 mmol, 1.0 equiv, Sigma M70800) and 2.4 mL of triethylamine (17.2 mmol, 3.0 equiv, Sigma T0886) were dissolved in 20 mL of dichloromethane. The mixture was put in the addition funnel and added dropwise to the reaction over a 1-hour period. After 4 hours the solvent was removed, and the residue was dissolved in 25 mL of saturated aqueous ammonium carbonate and stirred overnight. The reaction was washed with dichloromethane, and the aqueous layer was concentrated under vacuum. The crude material was purified by preparative HPLC (10:90 ACN: 0.05% triethylamine (TEA) in water, gradient to 90:10 over 60 minutes, monitoring at 254 nm). The combined fractions were frozen and lyophilized to give the product as a white powder with a yield of 20%. NMR results are as follows. $^1$H NMR (600 MHz, CDCl$_3$) δ 7.64 (ddd, J=11.1, 6.0, 4.4 Hz, 2H), 7.40 (ddd, J=8.3, 4.1, 2.1 Hz, 2H), 7.26 (dd, J=9.1, 5.9 Hz, 1H), 5.99 (d, J=9.0 Hz, 1H), 3.09 (q, J=7.3 Hz, 8H), 2.19 (d, J=4.5 Hz, 3H), 1.23 (t, J=7.3 Hz, 12H). An exemplary HPLC trace is provided in FIG. 10 and nuclear magnetic resonance traces are exemplified in FIG. 11 ($^1$H) and FIG. 12 ($^{13}$C).

Example 2

Figure 4:
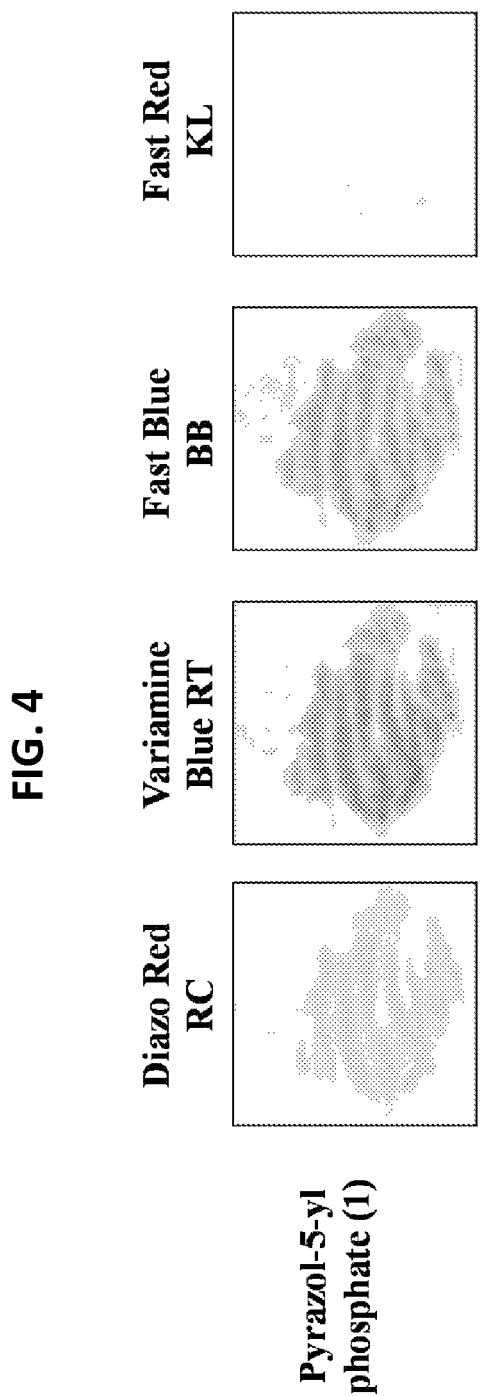
FIG. 4 is a series of photographs of Ki-67 staining on tonsil tissue with a variety of diazonium salts.

Immunohistochemical Detection of Targets in Tonsil Tissues with Various Diazonium Salts FIG. 4 is a series of images showing IHC detection of Ki-67 protein on tonsil tissue visualized using compound 1 and five different diazonium salts. The IHC staining was performed on a Benchmark XT with Ventana Medical System, Inc. reagents, using a modified version of the standard AP Red detection protocol for Ki-67. Basically, formalin-fixed, paraffin-embedded tonsil tissue was incubated with primary antibody CONFIRM anti-Ki67 (30-9) (VMSI 790-4286) for 16 minutes. UltraView Universal AP Red Multimer (VMSI 253-4327) was added and tissues were incubated for an additional 12 minutes. The detection reagents were manually titrated as follows: 100 uL of a 10 mM solution of compound 1 added, directly followed by 100 uL of the diazonium salt solution (5 mM), followed by incubation for 12 minutes. Five diazonium salt solutions were screened: Fast Red KL, Fast Red B, Diazo Red RC, Variamine Blue RT and Fast Blue BB. The slides were washed in a very dilute Dawn/water solution (one drop of Dawn dishwashing liquid in 50-100 mL of water), oven dried at 55° C. for 15 minutes and coverslipped.

Example 3

Figure 5:
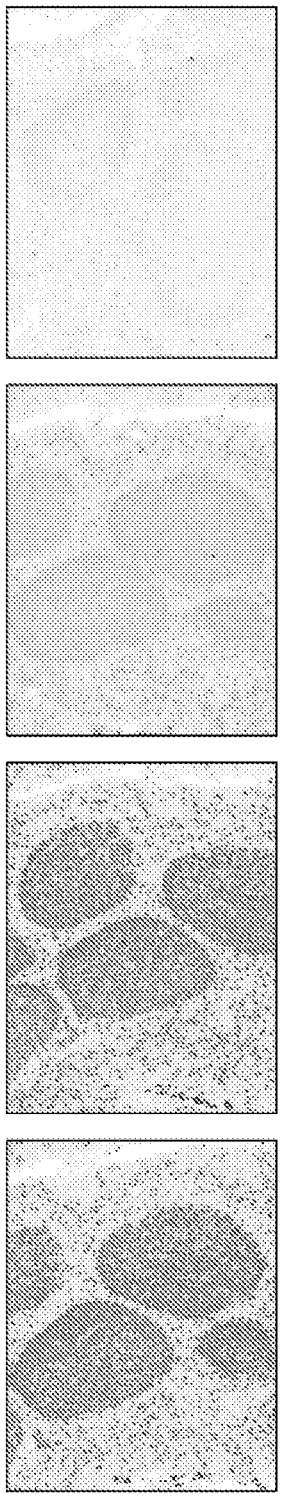
FIG. 5 is a series of photographs demonstrating the effect of diluting the diazonium concentration (the concentration of 1 was held at 10 mM).
Figure 6:
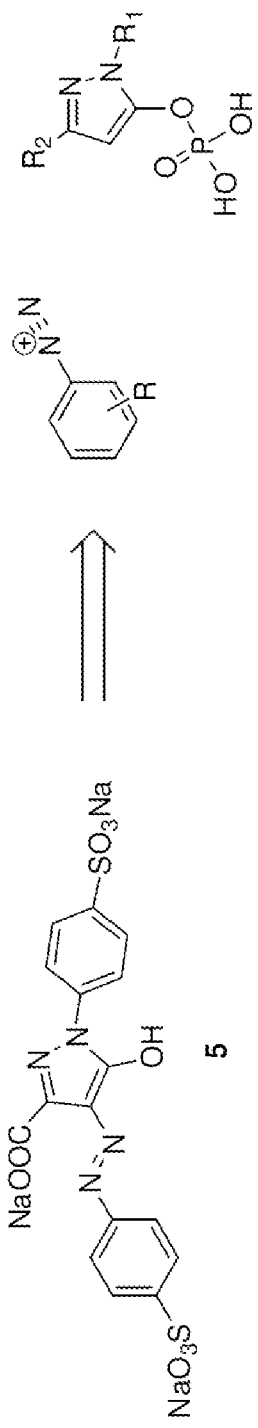
FIG. 6 is a retrosynthetic scheme for tartrazine (5).

Immunohistochemical Detection of Targets in Tonsil Tissues with an Exemplary Diazonium Salt FIG. 5 is a series of images showing IHC detection of Ki-67 protein on tonsil tissue visualized using a constant concentration of compound 1 (10 mM) and varying concentrations of Fast Blue BB: 10 mM, 5 mM, 2.5 mM, and 1 mM. The IHC staining was performed on a Benchmark XT with Ventana reagents, using a modified version of the standard AP Red detection protocol for Ki-67. Basically, formalin-fixed, paraffin-embedded tonsil tissue was incubated with the primary antibody CONFIRM anti-Ki67 (30-9) (VMSI 790-4286) for 16 minutes. UltraView Universal AP Red Multimer (VMSI 253-4327) was added to the tissues and the slides were incubated for an additional 12 minutes. The detection reagents were manually titrated as follows: 100 uL of a 10 mM solution of compound 1 added, directly followed by 100 uL of the Fast Blue BB solution (10, 5, 2.5, or 1 mM) was added to the tissues and the tissues were incubated for 12 minutes. The slides were washed in a very dilute Dawn/water solution, oven dried at 55° C. for 15 minutes and coverslipped.

Example 4

Figure 7:
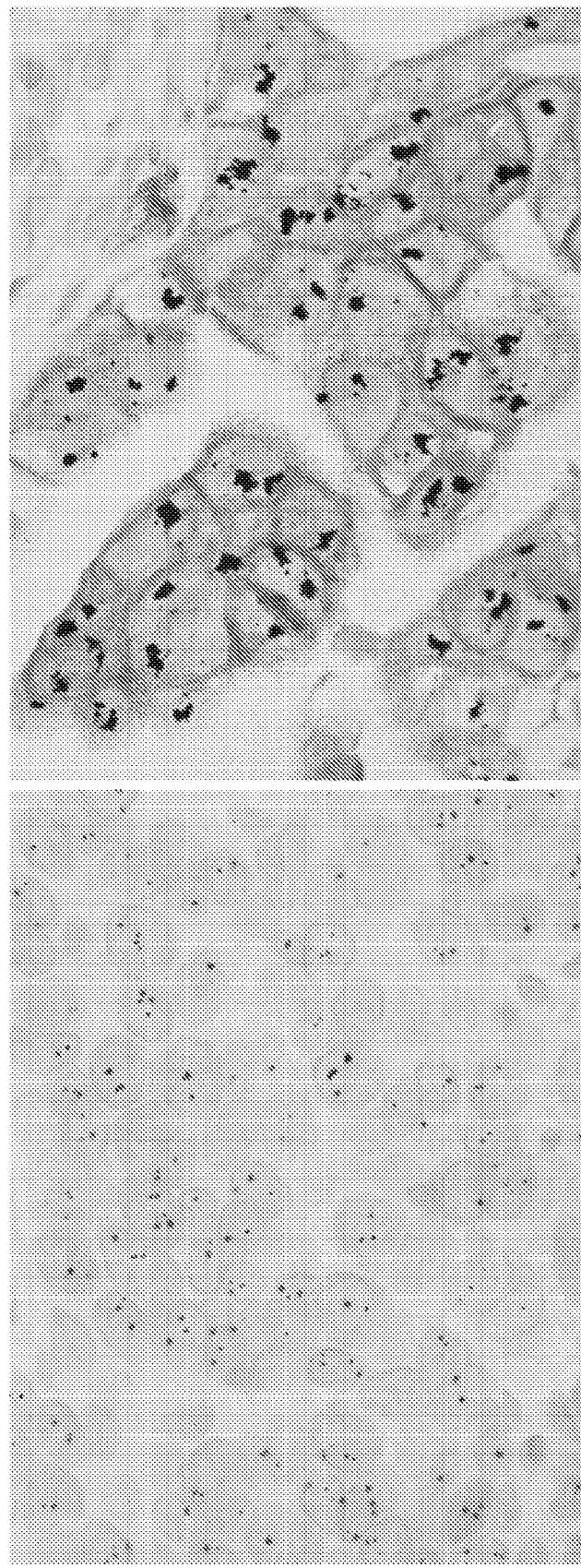
FIG. 7 is two brightfield images demonstrating multiple target detection on Xenografts: HER2 IHC (gold AP detection), HER2 ISH (silver detection), and CEN17 ISH (red AP detection).

Immunohistochemistry and In Situ Hybridization Detection of Targets in Xenograft Tissues FIG. 7 shows the brightfield multiple target detection on MCF7 and Calu-3 xenografts. The multiple target staining was performed on a Benchmark XT with Ventana reagents on HER23-in-1 Xenograft Control Slides (VMSI 783-4332). The IHC protein target was detected first using Ventana's PATHWAY anti-HER-2/neu (clone 4B5, VMSI 790-100) and visualized with the yellow/gold AP detection reagents described previously. Subsequently the gene target was detected with INFORM HER2DNA Probe (VMSI 780-4332) and visualized with ultraView SISH Detection Kit (VMSI 780-001). The Chromosome 17 Centromere was detected with INFORM Chromosome 17 Probe (VMSI 780-4331) and visualized with ultraView Alkaline Phosphatase Red Detection Kit (VMSI 760-501). The tissue was counterstained with Hematoxylin II (VMSI 790-2208) and Bluing Reagent (VMSI 760-2037), then washed with Dawn/water, air dried and coverslipped.

Example 5

Figure 8:
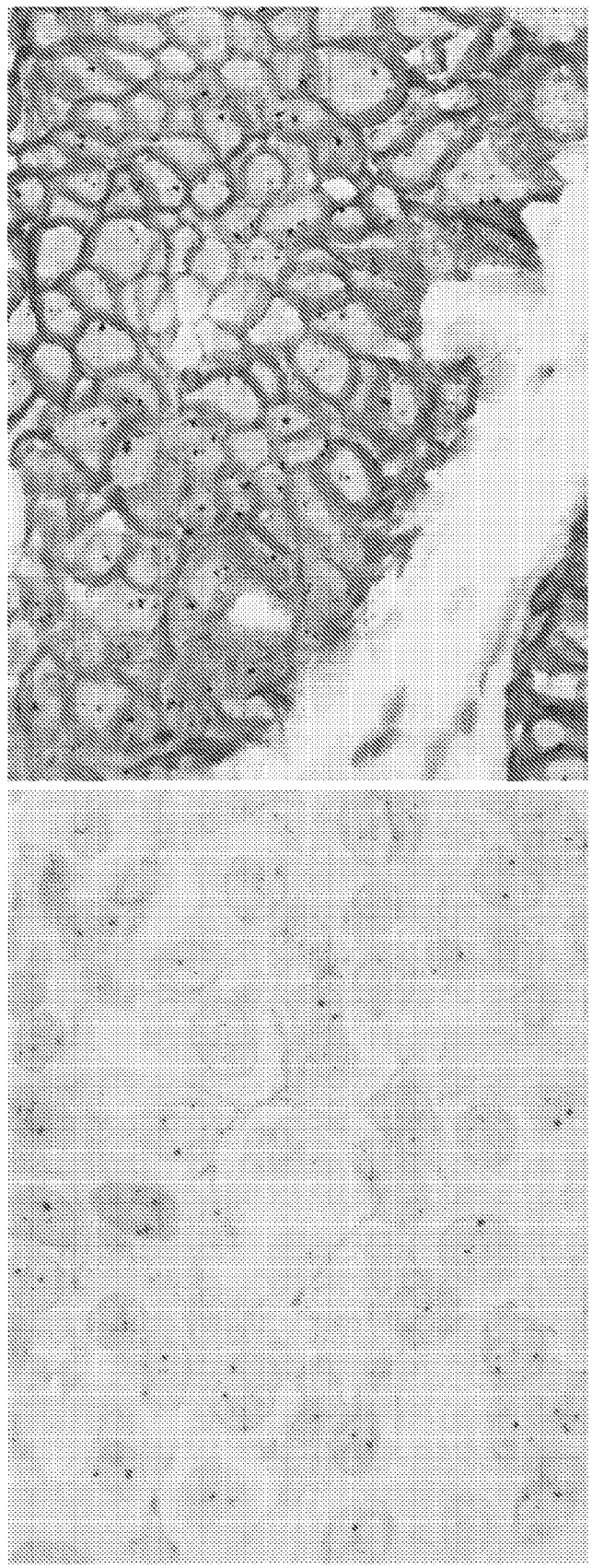
FIG. 8 is two brightfield images demonstrating multiple target detection on a clinical case: HER2 IHC (gold AP detection), HER2 ISH (silver detection), and CEN17 ISH (red AP detection).
Figure 9:
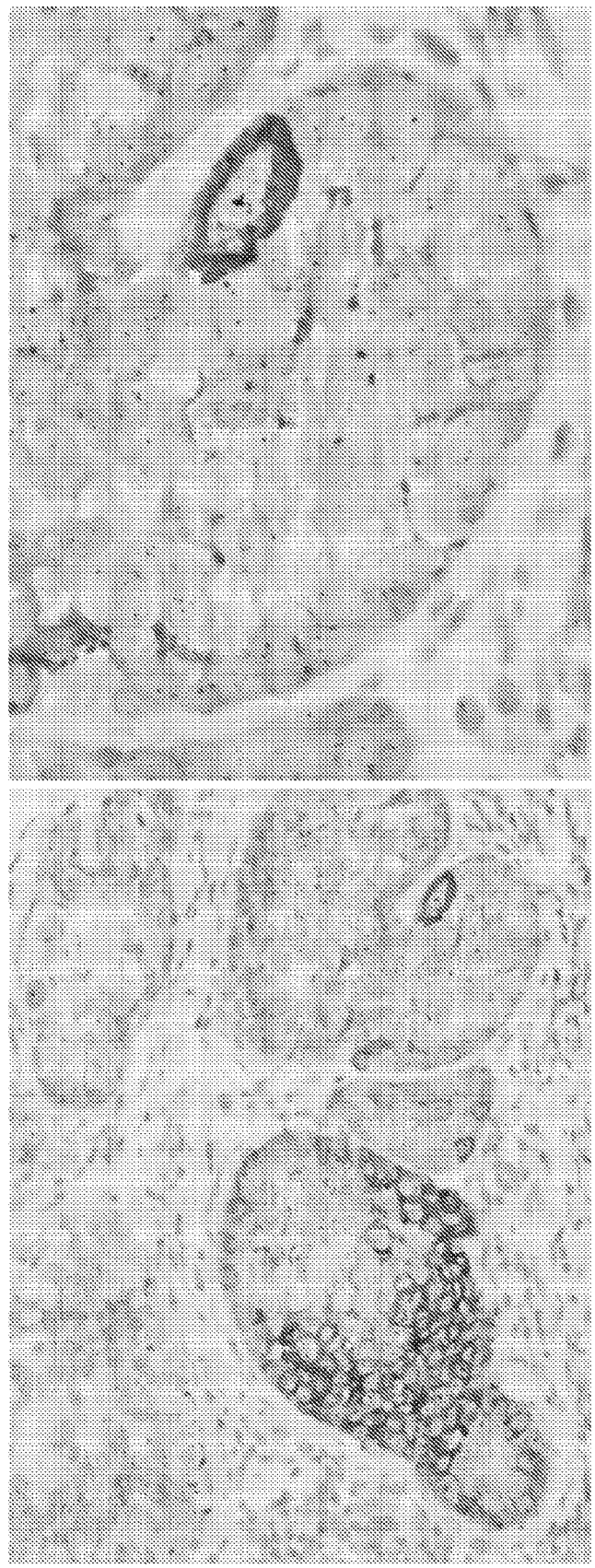
FIG. 9 is two brightfield images demonstrating multiple target detection on a clinical case: HER2 IHC (gold AP detection), HER2 ISH (silver detection), and CEN17 ISH (red AP detection).

Immunocytochemistry and In Situ Hybridization Detection of Targets in Human Clinical Specimens FIGS. 8 and 9 show the brightfield multiple target detection on two clinical cases (non-amplified and amplified HER2 gene). The multiple target staining was performed on a Benchmark XT with Ventana reagents on two clinical breast tissue samples. The IHC protein target was detected first using Ventana's PATHWAY anti-HER-2/neu (clone 4B5, VMSI 790-100) and visualized with the yellow/gold AP detection reagents described previously. Subsequently the gene target was detected with INFORM HER2DNA Probe (VMSI 780-4332) and visualized with ultraView SISH Detection Kit (VMSI 780-001). The Chromosome 17 Centromere was detected with INFORM Chromosome 17 Probe (VMSI 780-4331) and visualized with ultraView Alkaline Phosphatase Red Detection Kit (VMSI 760-501). The tissue was counterstained with Hematoxylin II (VMSI 790-2208) and Bluing Reagent (VMSI 760-2037), then washed with Dawn water, air dried and coverslipped.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of this invention are intended to be within the scope of the following claims.

We claim:
1. A compound having a formula:

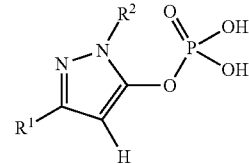

including salts thereof; and including both R and S enantiomeric forms and racemic mixtures thereof;
    wherein $R^1$ is selected from the group consisting of hydrogen, a halogen, an alkyl group, and an aryl group; and
    wherein $R^2$ is selected from the group consisting of hydrogen, an alkyl group, and an aryl group.
2. The compound of claim 1, wherein said halogen is selected from the group consisting of chlorine, fluorine, bromine and iodine.
3. The compound of claim 1, wherein $R^1$ is $CH_3$.
4. The compound of claim 1, wherein $R^2$ is phenyl.
5. The compound of claim 1, wherein said compound is described by the following formula:

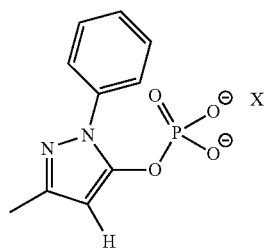

wherein X is two monovalent cations or one divalent cation.

6. The compound of claim 5, wherein said monovalent cation is selected from the group consisting of hydrogen, Na+, K+, or NH4+.

7. The compound of claim 5, wherein said divalent cation is Mg2+.

8. The compound of claim 1, wherein said compound is:

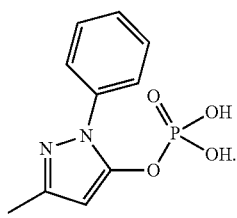 [SMILES: Cc1cc(OP(=O)(O)O)n(-c2ccccc2)n1]

9. A kit comprising:
a compound having a formula:

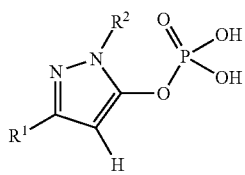

including salts thereof; and including both R and S enantiomeric forms and racemic mixtures thereof;
wherein R¹ is selected from the group consisting of hydrogen, a halogen, an alkyl group, and an aryl group; and
wherein R² is selected from the group consisting of hydrogen, an alkyl group, and an aryl group;
and
a diazonium salt.

10. The kit of claim 9, further comprising an enzyme that catalytically cleaves said compound.

11. The kit of claim 10, wherein said enzyme is a phosphatase.

12. The kit of claim 9, wherein said diazonium salt is 4-(benzoylamino)-2,5-diethoxybenzenediazotetra-chlorozincate (Fast Blue BB).

13. The kit of claim 10, wherein said enzyme is conjugated to a hapten.

14. The kit of claim 10, wherein said enzyme is conjugated to an antigen-binding protein.

15. The kit of claim 10, wherein said antigen-binding protein binds to a hapten.

16. The kit of claim 10, wherein said enzyme is conjugated to a nucleic acid.

17. The kit of claim 9, wherein said compound is

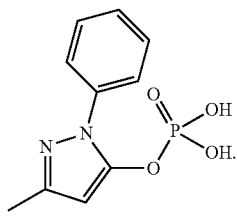 [SMILES: Cc1cc(OP(=O)(O)O)n(-c2ccccc2)n1]

18. A method of detecting a target in a biological sample comprising:
contacting said sample with a detection reagent comprising an enzyme that catalytically cleaves a compound having a formula:

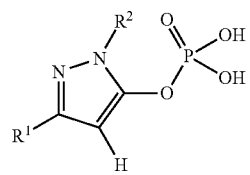

including salts thereof; and including both R and S enantiomeric forms and racemic mixtures thereof;
wherein R¹ is selected from the group consisting of hydrogen, a halogen, an alkyl group, and an aryl group; and
wherein R² is selected from the group consisting of hydrogen, an alkyl group, and an aryl group;
wherein said detection reagent directly or indirectly binds to said target, and a diazonium salt, wherein said enzyme catalytically cleaves said compound in the presence of said diazonium salt to produce a colored compound; and
detecting the presence of said colored compound.

19. The method of claim 18, wherein said enzyme is a phosphatase.

20. The method of claim 18, wherein said diazonium salt is 4-(benzoylamino)-2,5-diethoxybenzenediazotetra-chlorozincate (Fast Blue BB).

21. The method of claim 18, wherein said analyte is selected from the group consisting of a nucleic acid and a protein.

22. The method of claim 18, wherein said detection reagent comprises a first binding partner conjugated to said enzyme.

23. The method of claim 22, wherein said first binding partner is selected from the group consisting of an antigen-binding protein, a nucleic acid, and a hapten.

24. The method of claim 23, wherein said detection agent comprises an enzyme conjugated to a nucleic acid, said analyte is a nucleic acid, and said detection reagent hybridizes to said analyte.

25. The method of claim 23, wherein said detection agent comprises an enzyme conjugated to an antigen-binding protein, said analyte is a protein, and said detection reagent binds to said analyte.

26. The method of claim 23, wherein said detection is indirect and said detection agent comprises an enzyme conjugated to an antigen-binding protein specific for a hapten.

27. The method of claim 18, wherein said compound is:

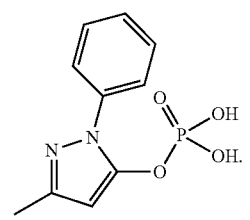 [SMILES: Cc1cc(OP(=O)(O)O)n(-c2ccccc2)n1]

* * * * *